(12) United States Patent
Umebayashi (10) Patent No.: US 11,931,230 B2
(45) Date of Patent: Mar. 19, 2024

(54) METHOD AND DEVICE FOR MANUFACTURING WAIST PART OF WEARABLE ARTICLE

(71) Applicant: ZUIKO CORPORATION, Osaka (JP)

(72) Inventor: Toyoshi Umebayashi, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 0 days.

(21) Appl. No.: 17/793,304

(22) PCT Filed: Dec. 15, 2020

(86) PCT No.: PCT/JP2020/046673
§ 371 (c)(1),
(2) Date: Jul. 15, 2022

(87) PCT Pub. No.: WO2021/153055
PCT Pub. Date: Aug. 5, 2021

(65) Prior Publication Data
US 2023/0051292 A1 Feb. 16, 2023

(30) Foreign Application Priority Data
Jan. 27, 2020 (JP) .................................. 2020-010633

(51) Int. Cl.
*A61F 13/15* (2006.01)
*A61F 13/49* (2006.01)

(52) U.S. Cl.
CPC .. *A61F 13/15723* (2013.01); *A61F 13/15699* (2013.01); *A61F 13/15804* (2013.01);
(Continued)

(58) Field of Classification Search
None
See application file for complete search history.

(56) References Cited

U.S. PATENT DOCUMENTS 6,589,638 B1 * 7/2003 McCormack ........ H01Q 15/141
156/290
6,712,922 B2 3/2004 Sorenson et al.
(Continued)

FOREIGN PATENT DOCUMENTS

JP 2015-521865 A 8/2015
JP 2016-120275 A 7/2016
(Continued)

OTHER PUBLICATIONS

International Search Report for corresponding Application No. PCT/JP2020/046673, dated Mar. 9, 2021.

*Primary Examiner* — Barbara J Musser
(74) *Attorney, Agent, or Firm* — Renner, Otto, Boisselle & Sklar, LLP (57) ABSTRACT

A method for manufacturing an around-torso portion of a worn article, including the steps of; intermittently conveying a plurality of first sheets by a first drum; conveying a preceding second sheet, of a plurality of second sheets, toward a junction with the first drum by a first pad of a second drum, and conveying the preceding second sheet so that the male touch fastener at the rear end of the preceding second sheet overlaps with the female touch fastener at the front end of one first sheet, of the plurality of first sheets; and conveying a subsequent second sheet, of the plurality of second sheets, toward the junction with the first drum by a second pad of the second drum, and conveying the subsequent second sheet so that the male touch fastener at the front end of the subsequent second sheet overlaps with the female touch fastener at the rear end of the one first sheet.

4 Claims, 7 Drawing Sheets

(52) U.S. Cl.
  CPC .... *A61F 13/4906* (2013.01); *A61F 13/15747* (2013.01); *A61F 2013/15878* (2013.01)

(56) References Cited

U.S. PATENT DOCUMENTS

| | | | |
|---|---|---|---|
| 6,783,487 B2 * | 8/2004 | Duhm | A61F 13/15756 493/194 |
| 7,425,242 B2 * | 9/2008 | Olsson | A61F 13/496 156/227 |
| 8,945,326 B2 | 2/2015 | Lavon et al. | |
| 9,750,647 B2 | 9/2017 | Umebayashi | |
| 9,999,549 B2 * | 6/2018 | LaVon | A61F 13/15756 |
| 2016/0159062 A1 | 6/2016 | Sablone | |

FOREIGN PATENT DOCUMENTS

| | | |
|---|---|---|
| JP | 2019-000638 A | 1/2019 |
| WO | 2014/006902 A1 | 1/2014 |

* cited by examiner

METHOD AND DEVICE FOR MANUFACTURING WAIST PART OF WEARABLE ARTICLE

TECHNICAL FIELD

The present invention relates to a method and a device for manufacturing an around-torso portion (waist part) of a worn article (wearable article).

BACKGROUND ART

Conventional techniques for stretchable sheets for around-torso portions of this type are known in the art, which include a female touch fastener and a male touch fastener that engage with each other in the front torso, wherein the tightness around the torso can be adjusted (the first and second patent documents).

CITATION LIST

Patent Document

[FIRST PATENT DOCUMENT] U.S. Pat. No. 6,712,922 B2 (FIG. 4)
[SECOND PATENT DOCUMENT] U.S. Pat. No. 8,945,326 B2 (FIG. 1)
[THIRD PATENT DOCUMENT] U.S. Pat. No. 9,750,647 B2

SUMMARY OF INVENTION

However, the conventional techniques fail to disclose the method for manufacturing the stretchable sheet.

On the other hand, the third patent document, identified above, discloses a method for manufacturing a worn article in which a male touch fastener on a stretchable sheet for an around-torso portion is attached to a female touch fastener on an absorbent body.

However, this prior document also fails to disclose a method for manufacturing a stretchable sheet with which attachment is achieved by means of the fasteners.

Thus, it is an object of the present invention to provide a novel and specific method and device for manufacturing a stretchable sheet for an around-torso portion of a worn article.

That is, the method of the present invention is a method for manufacturing an around-torso portion of a worn article, wherein:

the around-torso portion includes a plurality of first sheets each having a female touch fastener at a front end and a rear end thereof in a conveyance direction and a plurality of second sheets each having a male touch fastener at a rear end and a front end thereof in the conveyance direction, wherein the first sheets and the second sheets are arranged alternating and continuous with each other in the conveyance direction, the manufacturing method including the steps of:

intermittently conveying the plurality of first sheets by a first drum;

conveying a preceding second sheet, of the plurality of second sheets, toward a junction with the first drum by a first pad of a second drum, and conveying the preceding second sheet so that the male touch fastener at the rear end of the preceding second sheet overlaps with the female touch fastener at the front end of one first sheet of the plurality of first sheets; and conveying a subsequent second sheet, of the plurality of second sheets, toward the junction with the first drum by a second pad of the second drum, and conveying the subsequent second sheet so that the male touch fastener at the front end of the subsequent second sheet overlaps with the female touch fastener at the rear end of the one first sheet.

On the other hand, the device of the present invention is a device for manufacturing an around-torso portion of a worn article, wherein:

the around-torso portion includes a plurality of first sheets each having a female touch fastener at a front end and a rear end thereof in a conveyance direction and a plurality of second sheets each having a male touch fastener at a rear end and a front end thereof in the conveyance direction, wherein the first sheets and the second sheets are arranged alternating and continuous with each other in the conveyance direction, the manufacturing device including:

a first drum for intermittently conveying the plurality of first sheets; and a second drum for intermittently conveying the plurality of second sheets, the second drum including:

a first pad for conveying a preceding second sheet, of the plurality of second sheets, toward a junction with the first drum, and conveying the preceding second sheet so that the male touch fastener at the rear end of the preceding second sheet overlaps with the female touch fastener at the front end of one first sheet of the plurality of first sheets; and a second pad for conveying a subsequent second sheet, of the plurality of second sheets, toward the junction with the first drum, and conveying the subsequent second sheet so that the male touch fastener at the front end of the subsequent second sheet overlaps with the female touch fastener at the rear end of the one first sheet.

According to the present invention, the first sheets and the second sheets are attached together alternating with each other, thereby manufacturing a stretchable sheet.

DESCRIPTION OF EMBODIMENTS

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

First, before describing an embodiment of the present invention, a structure of a worn article 5 will be described with reference to the drawings.

Figure 1A:
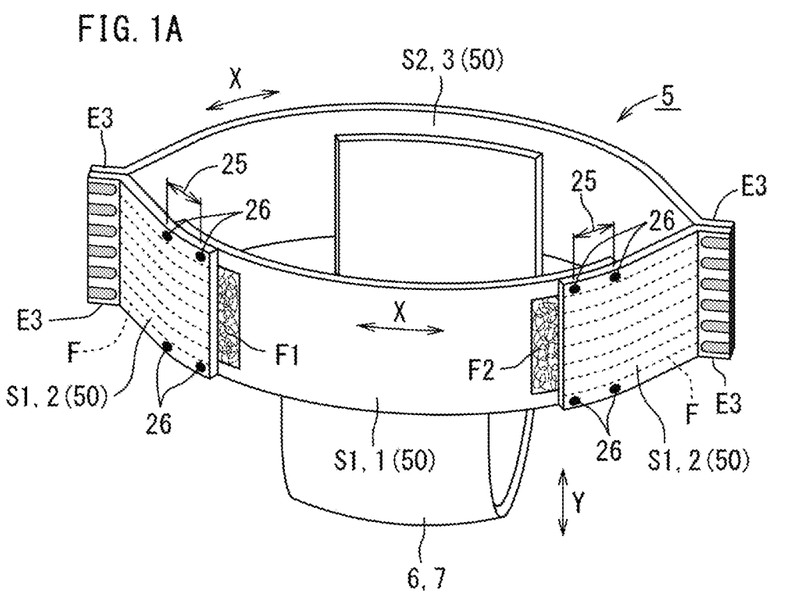
FIG. 1A is a schematic perspective view showing an example of a worn article to which the present invention is applied.
Figure 1B:
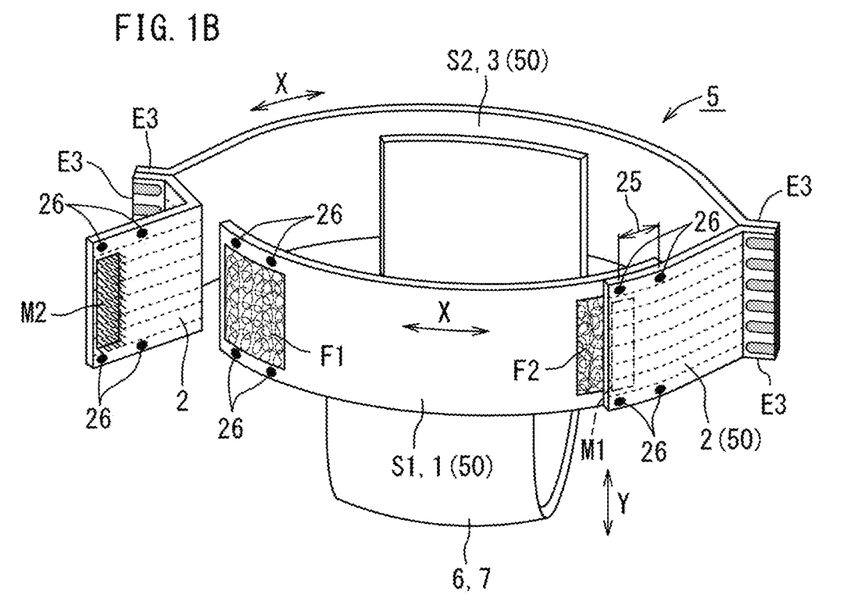
FIG. 1B is a schematic perspective view showing the worn article, with the male touch fastener of the second sheet detached from the female touch fastener of the first sheet.

As shown in FIG. 1A and FIG. 1B, the worn article 5 has a left-right symmetric shape and structure, and includes an absorbent body 6 and front and rear around-torso portions 50. The absorbent body 6 includes a front portion that covers the front torso of the wearer and extends in the girth direction X, a rear portion that covers the rear torso of the wearer and extends in the girth direction X, and a crotch portion 7 that covers the crotch therebetween.

The crotch portion 7 extends in the length direction Y perpendicular to the girth direction X. The absorbent body 6 forms a part or whole of the crotch portion 7.

As shown in FIG. 1A, in a final product, the crotch portion 7 is folded in two along a line that is parallel to the girth direction X. Thus, end portions E3 of the front and rear around-torso portions 50 in the girth direction X overlap with each other. The present worn article is of the pants type, and the end portions E3 of the front and rear around-torso portions 50, 50 in the girth direction X are welded to each other.

The absorbent body 6 is provided with an absorbent core (not shown). The absorbent core absorbs body fluids. The absorbent core is sandwiched between the top sheet and the back sheet. The sheets and the absorbent core are layered on each other.

The top sheet is made from a thin, liquid-permeable non-woven fabric and covers the skin-contact surface of the absorbent core. Cuffs (not shown) may be provided on this top sheet.

The back sheet covers the non-skin-contact surface of the absorbent core and is made from a liquid-impermeable resin sheet. The around-torso portions 50 are bonded to the end portions of the absorbent body 6 in the length direction Y.

The around-torso portions 50 may be provided with elastic members F for fitting the worn article 5 to the wearer. The elastic members F may be provided only in one or more of the around-torso portions 50.

For example, as the elastic members F, a plurality of rubber threads, rubber tapes, or a material including a thermoplastic resin may be employed. The elastic members F may be nullified (so that they exert no contraction force) in an area where they overlap with the absorbent body 6. The elastic members F may extend parallel to each other in the girth direction X.

The absorbent body 6 may be formed with around-leg portions (not shown), which are narrowed so as to conform to the legs of the wearer. Other elastic members made from rubber threads, or the like, for example, may be provided in the around-leg portions or in areas of the around-torso portions 50 that are continuous with the around-leg portions so as to conform to the legs of the wearer.

The absorbent body 6 is attached to the skin-contact surface of the around-torso portion 50.

In the present specification, the "skin-contact surface" refers to a surface that opposes the skin of the wearer when the worn article 5 is worn, the "non-skin-contact surface" refers to a surface that is opposite to the skin-contact surface.

Next, front and rear stretchable sheets S1, S2 forming the front and rear around-torso portions 50 will be described.

The around-torso portion 50 includes the first and second stretchable sheets S1, S2 for the front and rear torso portions.

The first stretchable sheet S1 is obtained by attaching together a first sheet 1 and a pair of second sheets 2. The second stretchable sheet S2 is made from a third sheet 3. First to third sheets 1 to 3 may be a laminate that is obtained by sandwiching elastic strands between two webs.

As shown in FIG. 1A and FIG. 1B, the first sheet 1 is arranged at the center of the front torso, and includes female touch fasteners F1, F2 at opposite ends in the girth direction X. On the other hand, the second sheet 2 is arranged on the left and right of the front torso, and includes, at one end, male touch fasteners M1 (see FIG. 2), M2 that engage with the female touch fasteners F1, F2.

In FIG. 1A, one end of the first sheet 1 that includes the female touch fastener and one end of the second sheet 2 that includes the male touch fastener together form an overlap portion 25 where they overlap with each other. The overlap portion 25 is formed with one or a plurality of tentative fastening portions 26 at which the first sheet 1 and the second sheet 2 are attached together. In the tentative fastening portions 26, the sheets 1, 2 may be lightly attached together so that they can be detached from each other, and the sheets 1, 2 may be attached together by a glue or an adhesive (e.g., a hotmelt adhesive) as well as thermal welding.

The other end of the second sheet 2 is welded to the third sheet 3. Therefore, the present worn article is a so-called re-closable, pants-type, disposable worn article. That is, the wearer can wear it as pants as shown in FIG. 1A, and can wear it while adjusting the tightness around the torso by detaching the male touch fasteners M1 (see FIG. 2), M2 of the second sheet 2 from the female touch fasteners F1, F2 of the first sheet 1 as shown in FIG. 1B. Note that the tentative fastening portions 26 are detached when the fasteners are detached from each other.

Next, a method and a device for manufacturing the first stretchable sheet S1 will be described.

Figure 2:
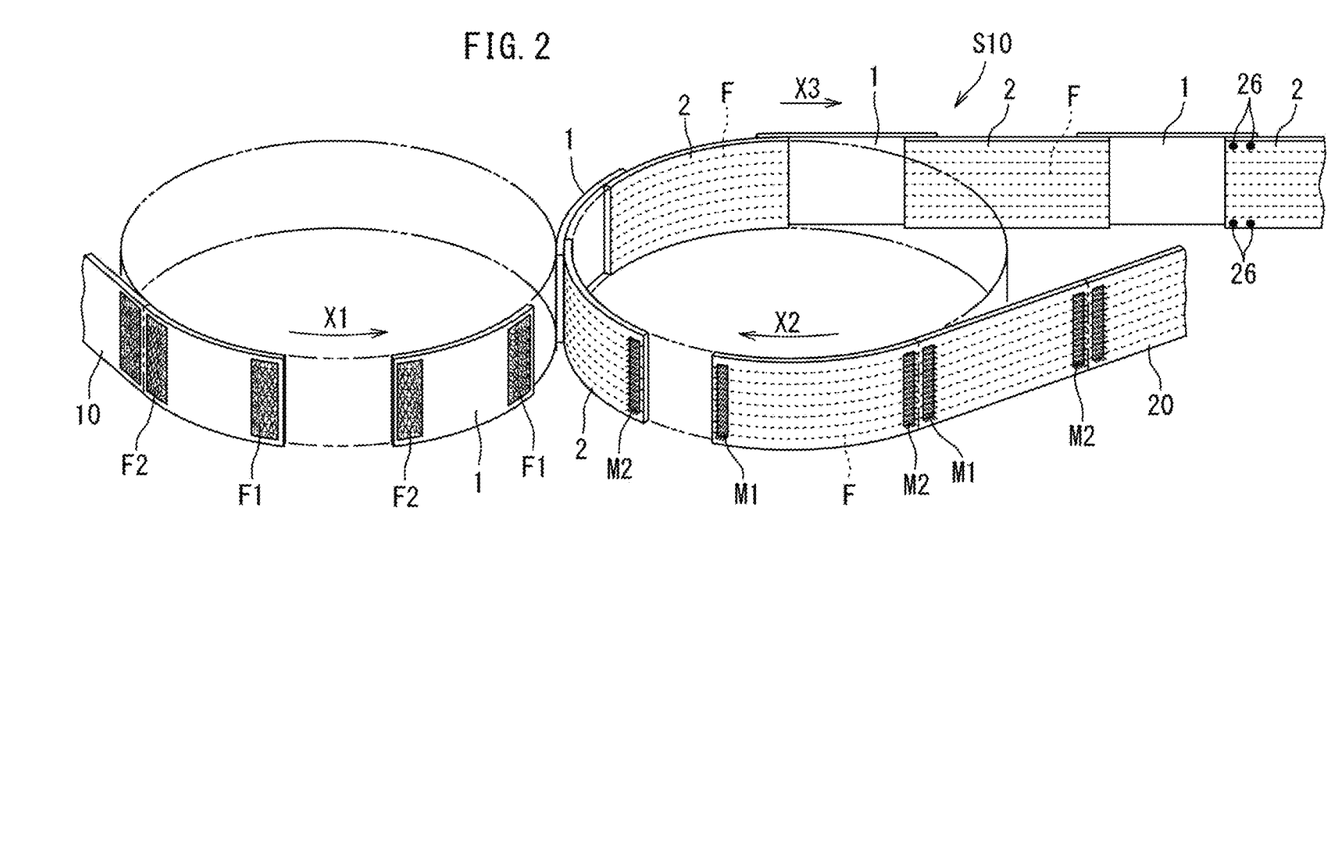
FIG. 2 is a schematic perspective view showing one embodiment of a method for manufacturing a stretchable sheet for an around-torso portion.

The first stretchable sheet S1 is produced from a first continuous stretchable sheet S10 including a plurality of first sheets 1, 1, which have the female touch fasteners F1, F2 at the front end and the rear end in the conveyance direction X1, and a plurality of second sheets 2, 2, which have the male touch fastener M1, M2 at the rear end and the other end in the conveyance direction X2, that are alternately arranged to be continuous in the conveyance direction X3, as shown in FIG. 2.

Figure 3:
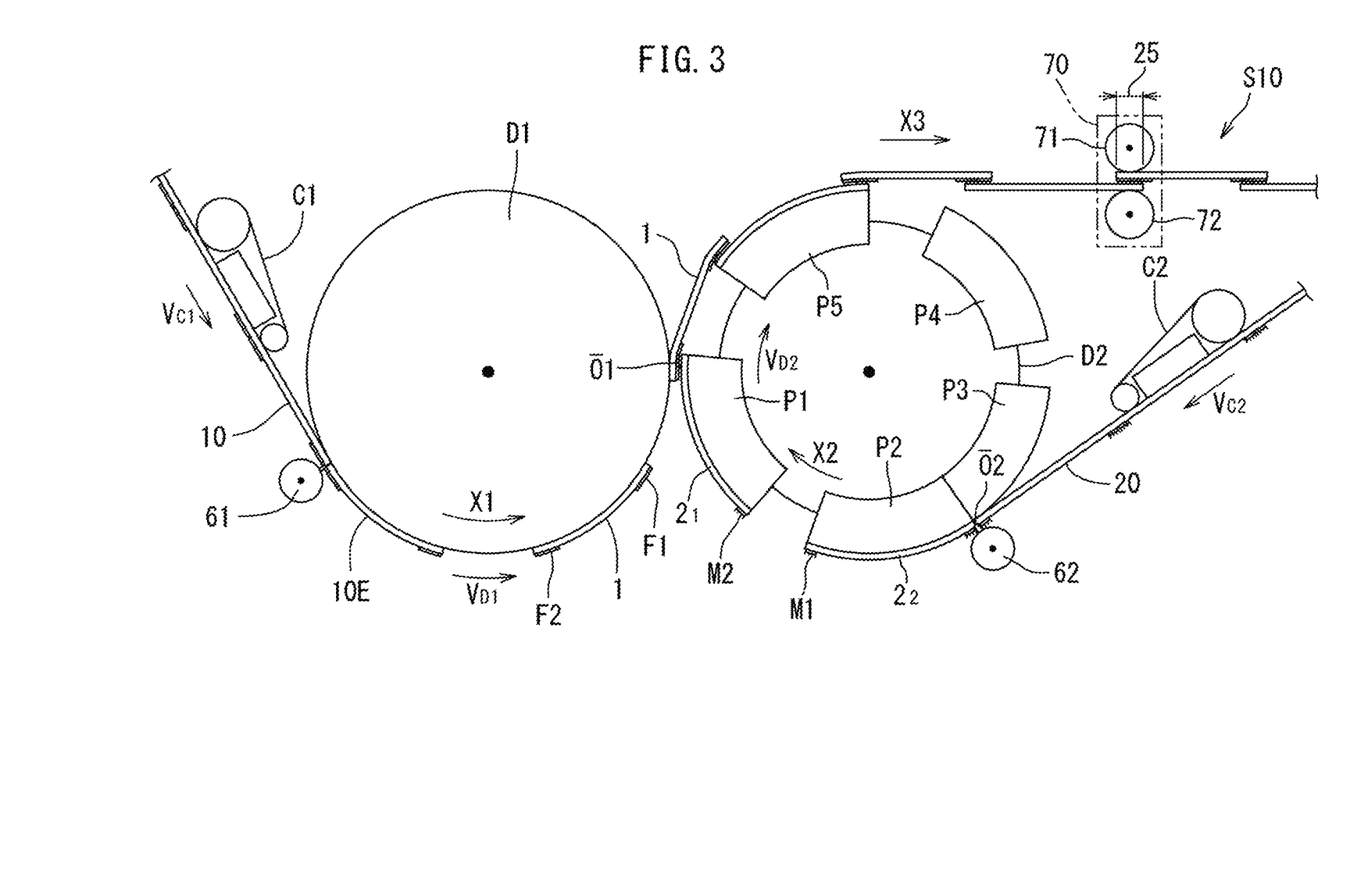
FIG. 3 is a front view showing one embodiment of a manufacturing device.

As shown in FIG. 3, the device for manufacturing the around-torso portion (the first stretchable sheet S1 (FIG. 1A)) includes a first drum D1 for intermittently conveying a plurality of first sheets 1, 1 and a second drum D2 for intermittently conveying a plurality of second sheets $2_i$. Note that in the description below, for the sake of description, figures in subscript will be used as reference signs for the second sheet.

The first drum D1 conveys first sheets 1, one after another, that are severed to a predetermined length from a first continuous sheet 10 by using cut and slip well known in the art. On the other hand, the second drum D2 is a repitch drum well known in the art that conveys second sheets $2_i$, one after another, that are severed to a predetermined length from a second continuous sheet 20.

A first control conveyor C1 for supplying the first continuous sheet 10 at a velocity $V_{C1}$ is provided upstream of the first drum D1. On the other hand, the first drum D1 rotates at a circumferential velocity $V_{D1}$ greater than the velocity $V_{C1}$. The first drum D1 is provided with vacuum sections (not shown), and the first drum D1 sucks on and holds the tip portion 10E while slipping against a tip portion 10E of the first continuous sheet 10. When the length of the tip portion 10E in the conveyance direction becomes equal to a predetermined length, a first cutter 61 severs the tip portion 10E, thus producing first sheets 1 one after another.

The produced first sheets 1 each move away from the tip of the first continuous sheet 10 at a velocity difference ($V_{D1}-V_{C1}$), and are intermittently conveyed by the first drum D1 toward the junction O1 with the second drum D2 at a constant pitch.

On the other hand, a second control conveyor C2 for supplying the second continuous sheet 20 at a velocity $V_{C2}$ is provided upstream of the second drum D2. The second drum D2 includes a few pads P1 to P5. The pads P1 to P5 revolve at a non-uniform velocity, which becomes equal to the velocity $V_{C2}$ of the second control conveyor C2 at the severing position O2 of a second cutter 62, and becomes equal to the velocity $V_{D2}$, which is greater than the velocity $V_{C2}$, at the junction O1. The pads P1 to P5 repeatedly accelerate and decelerate to move away from, and closer to, each other.

The second cutter 62 is arranged at the severing position O2. The second cutter 62 severs the second continuous sheet 20 into second sheets 2 at the edge of the pads P2, P3, which are adjacent to or in contact with each other in the circumferential direction of the second drum D2. Each pad conveys a severed second sheet 2 while sucking on and holding the second sheet 2 and while increasing the velocity toward the junction O1.

In FIG. 3, a preceding first pad P1 conveys one (preceding) second sheet $2_1$ toward the junction O1, and conveys the one second sheet $2_1$ so that the male touch fastener M2 at the rear end of one second sheet $2_1$ overlaps with the female touch fastener F1 at the front end of one first sheet 1.

A subsequent second pad P2 conveys another (following the one second sheet) second sheet $2_2$ toward the junction O1, and conveys another second sheet $2_2$ so that the male touch fastener M1 at the front end of the other second sheet $2_2$ overlaps with the female touch fastener F2 at the rear end of the one sheet 1.

Figure 5:
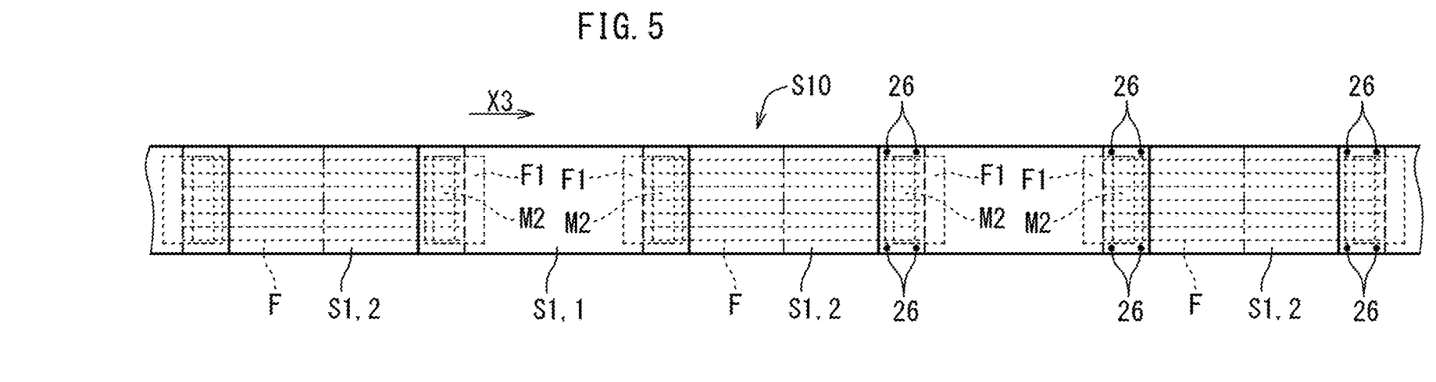
FIG. 5 is a plan view showing one embodiment of a method for manufacturing a stretchable sheet for an around-torso portion.

A tentative fastening device 70 may be provided downstream of the second drum D2. The tentative fastening device 70 includes a heating roller 71 and an anvil roller 72, for example. In a part of the overlap portion 25, the tentative fastening device 70 heats the first and second sheets 1, 2 to weld the sheets together. Thus, the first continuous stretchable sheet S10 shown in FIG. 5 is obtained.

Figure 4:
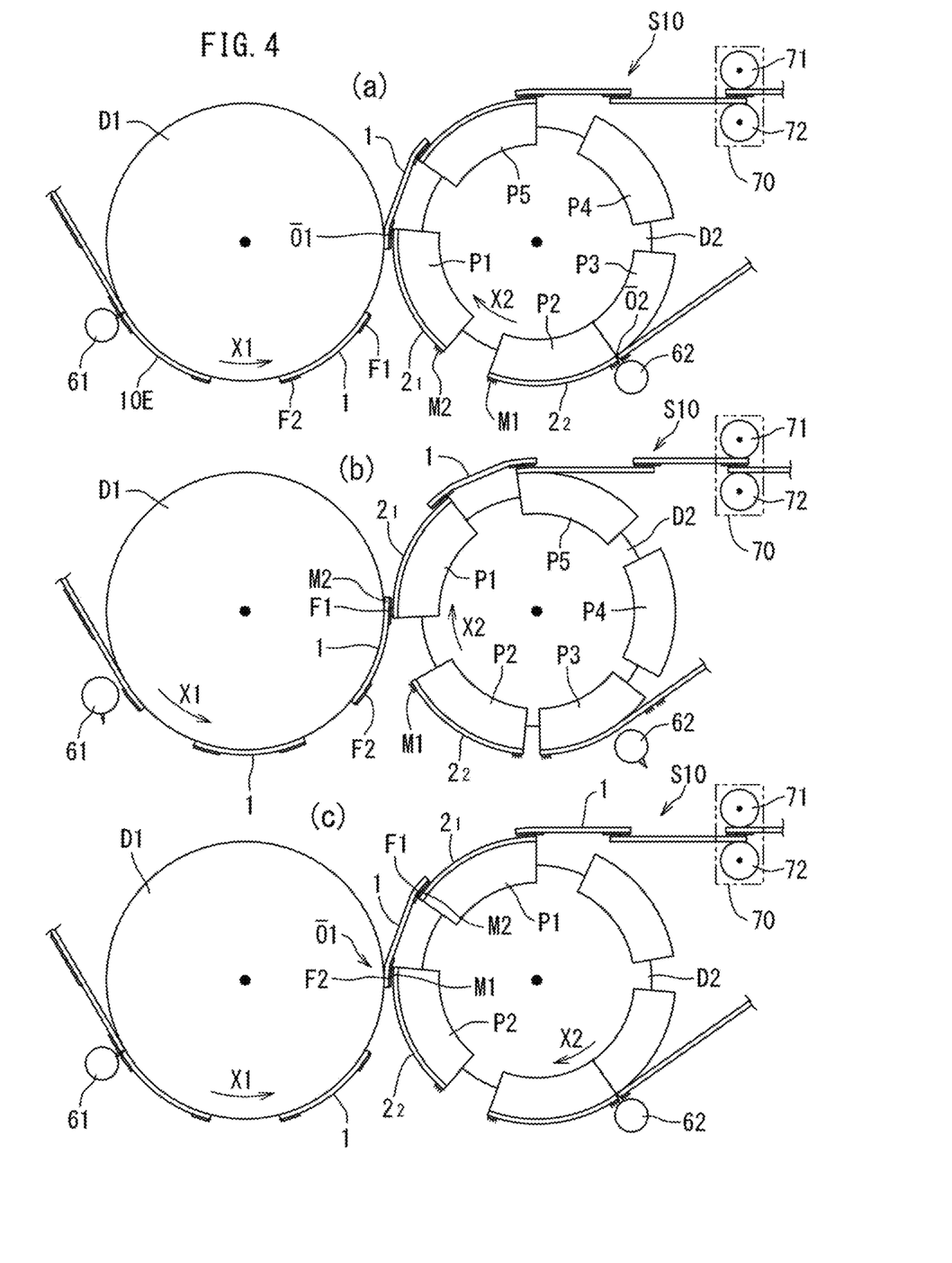
FIG. 4(a) to FIG. 4(c) are front views showing one embodiment of a manufacturing method.

Next, the details of the method for manufacturing the first stretchable sheet S1 will be described with reference to FIG. 4.

As shown in FIGS. 4(a) to 4(c), a plurality of first sheets 1, 1 are intermittently conveyed by the first drum D1.

One second sheet $2_1$, of a plurality of second sheets $2_i$, shown in FIG. 4(a) is conveyed by the first pad P1 of the second drum D2 toward the junction O1 on the first drum D1 with the first sheet 1, and the one second sheet $2_1$ is conveyed so that the male touch fastener M2 at the rear end of the one second sheet $2_1$ overlaps with the female touch fastener F1 at the front end of one first sheet 1, of a plurality of first sheets 1, 1, as shown in FIG. 4(b).

Then, as shown in FIG. 4(c), another second sheet $2_2$, of a plurality of second sheets $2_i$, is conveyed by the second pad P2 of the second drum D2 toward the junction O1 on the first drum D1 with the first sheet 1, and the second sheet $2_2$ subsequent to the one second sheet $2_1$ is conveyed so that the male touch fastener M1 at the front end of the subsequent second sheet $2_2$ overlaps with the female touch fastener F2 at the rear end of the one first sheet 1.

Thus, the first continuous stretchable sheet S10 is produced, wherein the first sheets 1, 1 and the second sheet $2_i$ are continuous with each other. The first continuous stretchable sheet S10 is conveyed by the second drum D2 with one second sheet $2_1$ of the first continuous stretchable sheet S10 being held on the first pad P1 and with the other second sheet $2_2$ of the first continuous stretchable sheet S10 being held on the second pad P2. Moreover, the first sheet 1 of the first continuous stretchable sheet S10, provided to bridge between the first pad P1 and the second pad P2, is conveyed by the second drum D2 to be supplied onto the tentative fastening device 70 downstream.

The end of the first sheet 1 and the end of the second sheet 2 supplied onto the tentative fastening device 70 are lightly welded together by heating a portion of the overlapping portion between the sheets between the heating roller 71 and the anvil roller 72.

Next, how the circumferential velocity of each of the pads P1 to P5 of FIG. 3 changes will be described.

The circumferential velocity of each of the pads P1 to P5 is at minimum at $V_{C2}$ when passing through the severing position O2, and the circumferential velocity is at maximum at $V_{D2}$ since when the front end of the pad reaches the junction O1 until the rear end of the pad passes through the junction O1.

Each pad accelerates after passing through severing position O2 until it reaches the junction O1. On the other hand, each pad decelerates after passing through the junction O1 until it reaches the severing position O2.

Thus, since each pad decelerates before the first pad P1 of FIG. 4(b) reaches the position of the first pad P1 of FIG. 4(c), the first sheet 1 between the first pad P1 and the second pad P2 slackens. Therefore, the engagement between the fasteners will not be disengaged.

As shown in FIG. 4(c), the first sheet 1, which has slackened as described above, turns into a linear shape and into a bent shape in the vicinity of the female touch fasteners F1, F2, and there is a force to attach the female touch fasteners F1, F2 to the male touch fastener M2, M1 even after being pressed between the drums.

Figure 6:
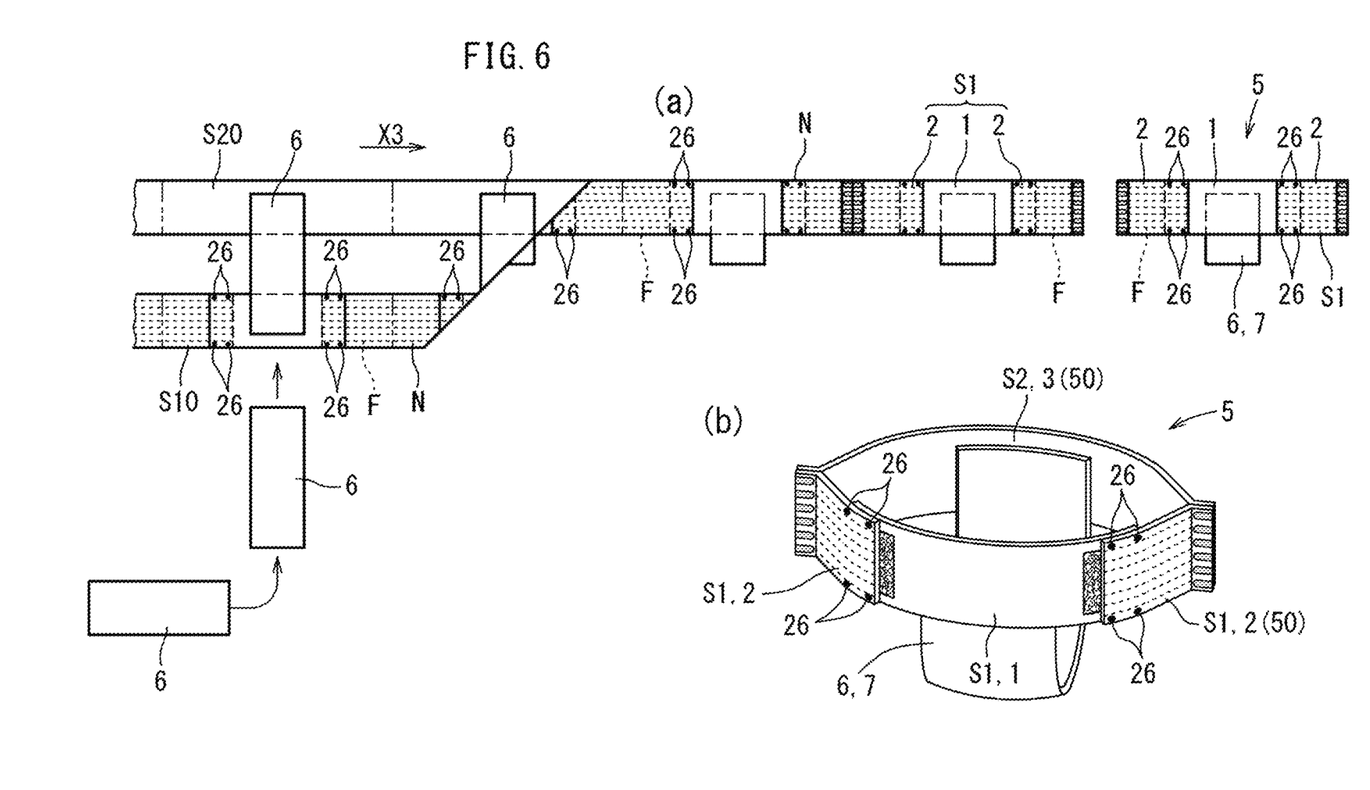
FIG. 6(a) is a schematic plan view showing an example of a method for manufacturing a worn article.
FIG. 6(b) is a schematic perspective view showing a worn article manufactured by the manufacturing method.

Next, a method for manufacturing a worn article using the first continuous stretchable sheet S10 will be described with reference to FIG. 6.

As shown in FIG. 6(a), a second continuous stretchable sheet S20 including second stretchable sheets S2 (FIG. 1) continuous with one another in the conveyance direction X3 and the first continuous stretchable sheet S10 are conveyed parallel to each other. The absorbent body 6 is provided to bridge between the first continuous stretchable sheet S10 and the second continuous stretchable sheet S20 in this state, thereby producing a continuous laminate N.

After the bridging, the continuous laminate N is folded in two in the area of the absorbent body 6 so that the first continuous stretchable sheet S10 and the second continuous stretchable sheet S20 oppose each other. Then, the first continuous stretchable sheet S10 and the second continuous stretchable sheet S20 are welded (sealed) together in areas corresponding to the opposite ends of the worn article 5 so that the continuous laminate N is divided in the unit of worn articles 5. After the welding, the continuous laminate N is cut off into individual worn articles 5 one after another. The produced worn article 5 can be worn as pants as shown in FIG. 5(b).

Figure 7:
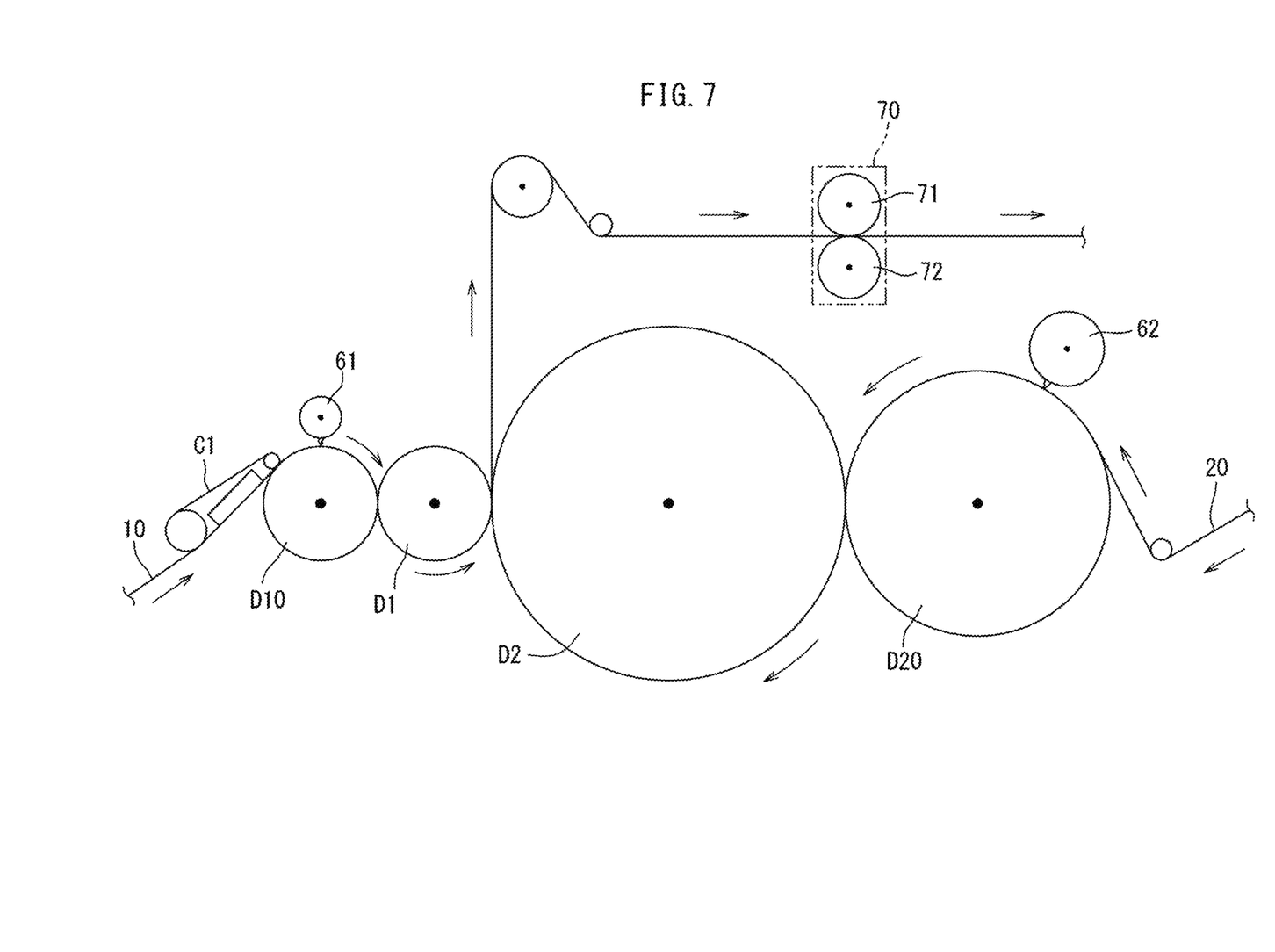
FIG. 7 is a front layout view showing another embodiment of a manufacturing device.

FIG. 7 schematically shows another embodiment of the manufacturing device.

In the present embodiment, a first upstream drum D10 is arranged upstream of the first drum D1, and a second upstream drum D20 is arranged upstream of the second drum D2.

The first cutter 61 is arranged in the vicinity of the first upstream drum D10, and the second cutter 62 is arranged in the vicinity of the second upstream drum D20.

The first control conveyor C1 is arranged upstream of the first upstream drum D10.

The tentative fastening device 70 is arranged downstream of the first and second drums D1, D2.

A method for manufacturing the first sheet according to the present embodiment will now be outlined.

The first continuous sheet 10 is supplied from the first control conveyor C1 onto the first upstream drum D10, and the first continuous sheet 10 is severed into individual first sheets by the first cutter 61 on the first upstream drum D10. The first upstream drum D10 conveys the first sheets, one after another, that are severed to a predetermined length from the first continuous sheet 10 by using cut and slip well known in the art.

The severed first sheets are handed over to the first drum D1. The first drum D1 may be a repitch drum well known in the art.

On the other hand, the second continuous sheet 20 is supplied onto the second upstream drum D20, and the second continuous sheet 20 is severed into individual second sheets by the second cutter 62 on the second upstream drum D20. The severed second sheets are handed over to the second drum D2. The second drum D2 is a repitch drum well known in the art, and conveys the second sheets, one after another, that are severed to a predetermined length.

The first and second sheets are engaged with each other between the first drum D1 and the second drum D2, thereby forming the first stretchable sheet. The first stretchable sheet is tentatively fastened in the overlapping portion between the first sheet and the second sheet by the tentative fastening device 70 downstream.

The embodiments described above primarily encompass an invention comprising elements as shown below.

One method of the invention is a method for manufacturing an around-torso portion of a worn article, wherein: the around-torso portion includes a plurality of first sheets having a female touch fastener at a front end and a rear end thereof in a conveyance direction and a plurality of second sheets having a male touch fastener at a rear end and a front end thereof in the conveyance direction, wherein the first sheets and the second sheets are arranged alternating and continuous with each other in the conveyance direction, the manufacturing method including the steps of: intermittently conveying the plurality of first sheets by a first drum; conveying a preceding second sheet, of the plurality of second sheets, toward a junction with the first drum by a first pad of a second drum, and conveying the preceding second sheet so that the male touch fastener at the rear end of the preceding second sheet overlaps with the female touch fastener at the front end of one first sheet of the plurality of first sheets; and conveying a subsequent second sheet, of the plurality of second sheets, toward the junction with the first drum by a second pad of the second drum, and conveying the subsequent second sheet so that the male touch fastener at the front end of the subsequent second sheet overlaps with the female touch fastener at the rear end of the one first sheet.

One device of the invention is a device for manufacturing an around-torso portion of a worn article, wherein: the around-torso portion includes a plurality of first sheets having a female touch fastener at a front end and a rear end thereof in a conveyance direction and a plurality of second sheets having a male touch fastener at a rear end and a front end thereof in the conveyance direction, wherein the first sheets and the second sheets are arranged alternating and continuous with each other in the conveyance direction, the manufacturing device including: a first drum for intermittently conveying the plurality of first sheets; and a second drum for intermittently conveying the plurality of second sheets, the second drum including: a first pad for conveying a preceding second sheet, of the plurality of second sheets, toward a junction with the first drum, and conveying the preceding second sheet so that the male touch fastener at the rear end of the preceding second sheet overlaps with the female touch fastener at the front end of one first sheet of the plurality of first sheets; and a second pad for conveying a subsequent second sheet, of the plurality of second sheets, toward the junction with the first drum, and conveying the subsequent second sheet so that the male touch fastener at the front end of the subsequent second sheet overlaps with the female touch fastener at the rear end of the one first sheet.

According to the manufacturing method and the manufacturing device, the first sheets and the second sheets are attached together alternating with each other, thereby producing a stretchable sheet for an around-torso portion.

In a preferred embodiment, the method further includes the steps of: conveying the preceding second sheet and the subsequent second sheet by the second drum with the preceding second sheet being held on the first pad and with the subsequent second sheet being held on the second pad; and conveying the one first sheet, provided to bridge between the first pad and the second pad, by the second drum.

With this method, since the first sheet is provided to bridge between the first pad and the second pad, an attachment force of fasteners is obtained with a high probability.

In a preferred embodiment, the manufacturing method further includes: a tentative fastening step of, in an overlapping portion between the first sheet including the female touch fastener and the second sheet including the male touch fastener, tentatively fastening the first sheet and the second sheet to each other by partially attaching the first sheet and the second sheet to each other.

Preferably, the tentative fastening step is performed when or after the fasteners overlap with each other.

In a preferred embodiment, the manufacturing device further includes a tentative fastening device for, in an overlapping portion between the first sheet including the female touch fastener and the second sheet including the male touch fastener, tentatively fastening the first sheet and the second sheet to each other by partially attaching the first sheet and the second sheet to each other.

In a more preferred embodiment, the tentative fastening device includes a heating roller and an anvil for heating a portion of the overlapping portion and welding the sheets together in the portion of the overlapping portion.

In these cases, the first sheet and the second sheet are not only attached to each other by touch fasteners, but are also tentatively fastened to each other in the overlapping portion by the tentative fastening step. This prevents a problem in which the first sheet and the second sheet are separated from each other while being conveyed.

Any feature illustrated and/or depicted in conjunction with embodiments or preferred embodiments may be used in the same or similar form in one or more of the other embodiments, and/or may be used in combination with, or in place of, features of the other embodiments.

While preferred embodiments have been described above with reference to the drawings, obvious variations and modifications will readily occur to those skilled in the art upon reading the present specification.

For example, the elastic members F may be absent on the first sheet or the second sheet of the first stretchable sheet. The female touch fastener may be formed by a non-woven fabric itself, which forms the first sheet, or may be obtained by bonding another female touch fastener member, which is different from the non-woven fabric, to a non-woven fabric.

Thus, such variations and modifications shall fall within the scope of the present invention as defined by the appended claims.

INDUSTRIAL APPLICABILITY

The present invention is applicable to a method and a device for manufacturing an around-torso portion of a worn article.

REFERENCE SIGNS LIST

1: First sheet, 1: One first sheet
10: First continuous sheet, 10E: Tip portion 2, $2_i$: First sheet, $2_1$: One (preceding) second sheet, $2_2$: Another (subsequent) second sheet
20: Second continuous sheet, 25: Overlapping portion, 26: Tentative fastening portion
3: Third sheet
5: Worn article, 50: Around-torso portion
6: Absorbent body, 7: Crotch portion
61: First cutter, 62: Second cutter
70: Tentative fastening device, 71: Heating roller, 71: Anvil
D1: First drum, D2: Second drum, P1 to P5: Pad, D10: First upstream drum, D20: Second upstream drum
E3: End portion, F: Elastic member, F1, F2: Female touch fastener, M1, M2: Male touch fastener
N: Continuous laminate
S1: First stretchable sheet, S2: Second stretchable sheet, S10: First continuous stretchable sheet
S20: Second continuous stretchable sheet
O1: Junction, O2: Severing position
X: Girth direction, Y: Length direction
X1 to X3: Conveyance direction

The invention claimed is:

1. A method for manufacturing an around-torso portion of a worn article, wherein:
the around-torso portion includes:
first sheets, each having a female touch fastener at a front end and a rear end thereof in a conveyance direction, the female touch fastener at the front end and the female touch fastener at the rear end being spaced apart from each other in the conveyance direction in each of the first sheets, and
second sheets, each having a male touch fastener at a rear end and a front end thereof in the conveyance direction, the male touch fastener at the rear end and the male touch fastener at the front end being spaced from each other in the conveyance direction in each of the second sheets,
wherein the first sheets and the second sheets are arranged alternating and continuous with each other in the conveyance direction, the manufacturing method comprising the steps of:
intermittently conveying the first sheets by a first drum;
conveying a preceding second sheet, of the second sheets, toward a junction with the first drum by a first pad of a second drum, and conveying the preceding second sheet so that the male touch fastener at the rear end of the preceding second sheet, which is spaced apart from the male touch fastener at the front end of the preceding second sheet, overlaps with the female touch fastener at the front end of one first sheet of the first sheets, which is spaced apart from the female touch fastener at the rear end of the one first sheet;
conveying a subsequent second sheet, of the second sheets, toward the junction with the first drum by a second pad of the second drum, and conveying the subsequent second sheet so that the male touch fastener at the front end of the subsequent second sheet, which is spaced apart from the male touch fastener at the rear end of the subsequent second sheet, overlaps with the female touch fastener at the rear end of the one first sheet, which is spaced apart from the female touch fastener at the front end of the one first sheet; and
tentatively fastening one of the first sheets and one of the second sheets to each other by partially attaching the one of the first sheets and the one of the second sheets to each other in a tentative attachment area,
the tentative fastening step performed in an overlapping portion between the one of the first sheets and the one of the second sheets, wherein the tentative attachment area excludes the female touch fastener at the front and rear ends and the male touch fastener at the rear and front ends,
conveying the preceding second sheet and the subsequent second sheet by the second drum with the preceding second sheet being held on the first pad and with the subsequent second sheet being held on the second pad, and
conveying the one first sheet, providing to bridge between the first pad and the second pad, by the second drum along a circumference of the second drum after exiting the junction.

2. The method for manufacturing the around-torso portion according to claim 1, wherein the tentative fastening step is performed when or after the female fastener and the male fastener overlap with each other.

3. A device for manufacturing an around-torso portion of a worn article, wherein:
the around-torso portion includes:
first sheets, each having a female touch fastener at a front end and a rear end thereof in a conveyance direction, the female touch fastener at the front end and the female touch fastener at the rear end being spaced apart from each other in the conveyance direction in each of the first sheets, and
second sheets, each having a male touch fastener at a rear end and a front end thereof in the conveyance direction, the male touch fastener at the rear end and the male touch fastener at the front end being spaced from each other in the conveyance direction in each of the second sheets,
wherein the first sheets and the second sheets are arranged alternating and continuous with each other in the conveyance direction, the manufacturing device comprising:
  a first drum for intermittently conveying the first sheets; and
  a second drum for intermittently conveying the second sheets, the second drum comprising:
  a first pad for conveying a preceding second sheet, of the second sheets, toward a junction with the first drum, and conveying the preceding second sheet so that the male touch fastener at the rear end of the preceding second sheet, which is spaced apart from the male touch fastener at the front end of the preceding second sheet, overlaps with the female touch fastener at the front end of one first sheet of the first sheets, which is spaced apart from the female touch fastener at the rear end of the one first sheet;
  a second pad for conveying a subsequent second sheet, of the second sheets, toward the junction with the first drum, and conveying the subsequent second sheet so that the male touch fastener at the front end of the subsequent second sheet, which is spaced apart from the male touch fastener at the rear end of the subsequent second sheet, overlaps with the female touch fastener at the rear end of the one first sheet, which is spaced apart from the female touch fastener at the front end of the one first sheet; and
  a tentative fastening device for tentatively fastening one of the first sheets and one of the second sheets to each other in a tentative attachment area by partially attaching the one of the first sheets and the one of the second sheets to each other in an overlapping portion between the one of the first sheets and the one of the second sheets,
  wherein the tentative attachment area excludes the female touch fastener at the front and rear ends and the male touch fastener at the rear and front ends,
  wherein the second drum is configured to convey the preceding second sheet with the preceding second sheet being held on the first pad and convey the subsequent second sheet with the subsequent second sheet being held on the second pad, and
  wherein the second drum is configured to convey the one first sheet, providing to bridge between the first pad and the second pad, along a circumference of the second drum after exiting the junction.

4. The device for manufacturing the around-torso portion according to claim 3, wherein the tentative fastening device includes a heating roller and an anvil for heating a portion of the overlapping portion and welding the one of the first sheets and the one of the second sheets together in the portion of the overlapping portion.

* * * * *